United States Patent [19]
Shultz et al.

[11] Patent Number: 5,981,235
[45] Date of Patent: Nov. 9, 1999

[54] METHODS FOR ISOLATING NUCLEIC ACIDS USING ALKALINE PROTEASE

[75] Inventors: John Shultz, Verona; Craig E. Smith, Oregon; Douglas R. Storts, Madison; Paula Brisco, Oregon; Judy Frederiksen, Oregon; Susanne Selman, Madison; Josephine Grosch, Mazomanie, all of Wis.

[73] Assignee: Promega Corporation, Madison, Wis.

[21] Appl. No.: 08/681,922

[22] Filed: Jul. 29, 1996

[51] Int. Cl.$^6$ ............... C12P 19/34; C12N 9/99; C12N 9/50
[52] U.S. Cl. ............... 435/91.1; 435/184; 435/219
[58] Field of Search ............... 435/87, 91.1, 259, 435/184, 219; 536/23.1, 127

[56] References Cited

U.S. PATENT DOCUMENTS

| | | | |
|---|---|---|---|
| 4,843,155 | 6/1989 | Chomczynski | 536/27 |
| 4,900,677 | 2/1990 | Hewitt | 435/259 |
| 5,075,430 | 12/1991 | Little | 536/27 |
| 5,155,018 | 10/1992 | Gillespie et al. | 435/91 |
| 5,386,024 | 1/1995 | Kacian et al. | 536/25.4 |
| 5,439,817 | 8/1995 | Shetty et al. | 435/222 |

FOREIGN PATENT DOCUMENTS

| | | |
|---|---|---|
| WO 95/06652 | 3/1995 | WIPO . |
| WO 96/09308 | 3/1996 | WIPO . |

OTHER PUBLICATIONS

Boom et al, *J. Clinical Microbiol.* 28(3):495–503 (1990).
Schoenfeld et al. in *Promega Notes* 53:12–21 (1995).
Von der Osten et al., *J. Biotechnol.* 28:55–68 (1993).
Aehle et al., *J. Biotechnol.* 28: 31–40 (1993).
Birnboim, H.C. 1983, *Methods in Enzymology,* vol. 100, pp. 243–255.
Birnboim, H.C. and Doly, J. 1979, *Nucleic Acids Res.,* vol. 7, pp. 1515–1523.
QIAGEN Protease, QIAGEN Product Guide 1996, p. 61.
Vogelstein, B. et al., *Proc. Natl. Acad. Sci USA,* vol. 76, No. 2, pp. 615–619 (1979).
Carter, M.J. et al., *Nucleic Acids Res.,* vol. 21, No. 4, p. 1044 (1993).
Taylor, R.G. et al., *Nucleic Acids Res.,* vol. 21, No. 7, pp. 1677–1678 (1993).

*Primary Examiner*—David M. Naff
*Attorney, Agent, or Firm*—Grady J. Frenchick; Michael Best & Friedrich LLP; Karen B. King

[57] ABSTRACT

Solutions containing nucleic acids are treated with an alkaline protease to digest proteins such as nucleases that degrade the nucleic acids. In the isolation of nucleic acids, a biological sample containing nucleic acids is suspended in a solution containing water, buffer and chelating agent, the pH of the solution is adjusted to at least about 10 by adding a solution of sodium hydroxide and anionic detergent, an alkaline protease is incubated in the solution until nucleases are degraded, the pH of the solution is lowered to reduce activity of the alkaline protease by adding a solution having a pH between 3.5 and 4.5 and the alkaline protease is heat inactivated. Lowering of the pH may produce a cloudy solution which is cleared by centrifuging. Nucleic acids are isolated from the cleared solution by alcohol precipitation, or by using paramagnetic particles or a resin matrix containing silica particles. A chaotropic salt can be used to reversibly bind DNA to the resin matrix.

24 Claims, 4 Drawing Sheets

METHODS FOR ISOLATING NUCLEIC ACIDS USING ALKALINE PROTEASE

FIELD OF THE INVENTION

The present invention relates to procedures for treating solutions of nucleic acids, including solutions generated in the process of isolating nucleic acid material from biological samples, so the nucleic acid material contained therein or isolated therefrom can be used for various purposes. Uses for solutions of the various types of nucleic acid materials isolated or treated according to the methods of this invention include enzymatic restriction digestion of a deoxyribonucleic acid (DNA) material of interest to clone, map, or engineer genes, DNA sequencing to identify the presence of a gene or mutation in a fragment of DNA, hybridization assays of ribonucleic acid (RNA) or of DNA for the diagnosis of genetically transmitted diseases, for the amplification of nucleic acids by the polymerase chain reaction (PCR) or other target amplification procedures for the identification of individuals for forensic or paternity purposes, or for the introduction of DNA into mammalian cells (transfection) for gene therapy or for research into gene expression. Specifically, one aspect of the present invention relates to fast, efficient procedures for ensuring that nucleic acid materials isolated from a biological sample are not degraded during the isolation procedure, or contaminated with deleterious proteins, such as nucleases. Another aspect of the present invention relates to fast, efficient procedures for treating a solution of a nucleic acid material to inactivate nucleases contained therein, wherein any active nucleases in the solution are capable of degrading the material.

BACKGROUND OF THE INVENTION

Many diagnostic, research, and development procedures require the isolation and detection of specific nucleic acid (DNA or RNA) sequences present in a biological sample. For example, nucleic acid detection methods are used to identify bacteria, viruses, or other microorganisms, whose presence can indicate the cause of an infectious disease. The nucleic acids of the cells of more complex organisms, such as the DNA of human white blood cells, are also more and more commonly isolated and tested in order to establish the presence of a mutation associated with cancer or a genetic disease. Nucleic acids isolated from samples of biological tissue, such as blood taken directly from an individual or from a crime scene, are also often used to determine the identity of the individual from which the sample originated, as, for example, for paternity or forensic work. Nucleic acids are also isolated from biological tissue in order to perform research and development procedures such as cloning and nucleic acid analysis techniques well known to one skilled in the art.

Before one can isolate a nucleic acid material for any of the purposes noted above, it is necessary to make available the specific nucleic acid of interest in a sample of biological material. Frequently, the nucleic acid will be contained within a bacteria cell, a fungal cell, a viral particle, or the cell of a more complex organism, such as a human white blood cell or a plant cell.

Such cells or particles can be treated chemically or enzymatically to dissolve or denature the walls of such organisms, causing the nucleic acids to be released. This process of dissolution is commonly referred to as "lysis". The resulting solution containing such lysed material is referred to as a "lysate".

Unfortunately, such release exposes nucleic acids to degradation by endogenous nucleases present in the sample, which may exist in such abundance that destruction of the nucleic acids begins immediately upon nucleic acid release. Any nucleases remaining at the end of any subsequent purification process can continue to degrade remaining intact nucleic acids until there is nothing useful left of the original sequence of each such nucleic acid molecule. Nucleases are abundant in most biological samples and are often extremely resistant to treatments which are known to inactivate other enzymes. Deoxyribonucleases (DNases) such as endonuclease I, are naturally produced in large quantities by many of the most popular strains of bacterial cells used in cloning, transformation, and testing of DNA today. See, for example, discussion and list of end A+ strains of *Escherichia coli* (*E. coli*) by Schoenfeld et al. in *Promega Notes* 53: 13–21 (1995). Ribonucleases (RNases) also are abundant in most, if not all, biological samples.

Other proteins released in the process of lysing biological material can usher in another set of problems. Endotoxins, a type of lipopolysaccharide modified protein released from many types of biological material, are toxic to animal tissue culture cells, and can kill target cells before a nucleic acid-containing sequence of interest can be transformed into the cells. Thus, endotoxins can render a solution of nucleic acids contaminated therewith useless for the transfection of tissue culture cells, as the cells must be kept alive to be of any use. In addition, endotoxins also cause complications in therapy including possible introduction of nucleic acids into live animals.

To deal with the problem of nucleases and other undesirable products released by lysis, it is common in the art to employ a variety of means to purify nucleic acids from a biological sample. For example, anionic detergents and chaotropic agents, such as guanidinium thiocyanate, have been used simultaneously to inactivate or to inhibit nuclease activities and to release nucleic acids from within cells and subcellular structures. Unfortunately, many such agents are also potent inhibitors of the enzymes used in many standard procedures such as restriction digestion, transformation, amplification, targeting, and hybridization procedures. As a result of all the above factors, it has become customary to use additional isolation steps to remove these agents to recover usable, substantially intact, nucleic acids.

One common procedure used to isolate nucleic acids from a lysate is to precipitate the nucleic acids out of the solution, using a low molecular weight alcohol. Because other macromolecules also precipitate under these conditions producing a sticky, intractable mass that entraps the nucleic acids, it has frequently been necessary to resort to extraction of the sample with hazardous organic solvent mixtures containing phenol, and/or chloroform prior to ethanol precipitation. In some cases when anionic detergents are used, proteases that are active in the presence of these detergents, such as proteinase K, are used to degrade partially protein components of the sample or to degrade components that may not be extracted by the solvent treatment.

It will be readily appreciated that the method of isolation cited above is tedious, hazardous, labor-intensive, and slow. If great care is not taken in performing the procedure, residual contamination with nucleases can occur, and the sample nucleic acids will be degraded or lost. Diagnostic tests performed with such samples can also give false negative results due to such degradation. False negative results can also be obtained due to chemical interference, for example from residual anionic detergents, chaotropic salts, or ethanol remaining in the sample and inhibiting target amplification procedures. If anionic detergents and proteases have been used, residual proteolytic activity can also degrade the enzymes used in target amplification and/or hybridization detection reactions and produce false negative results. Thus, such procedures are not well suited for routine processing of biological specimens received in clinical or forensic laboratories in any quantity.

Less tedious methods of isolating nucleic acids are also known. One such method commonly used to isolate and to purify RNA uses magnetic particles, such as paramagnetic particles, to isolate specific species of nucleic acids from a lysate solution containing guanidinium thiocyanate and an anionic detergent. See, for example, PolyATtract® mRNA Isolation Systems as described in Promega Corporation's 1996 Catalog, pp. 158–160; or see PCT Publication No. WO 96/09308. Another type of nucleic acid isolation method uses silica to isolate plasmid DNA from a bacterial lysate solution containing a guanidinium salt and a base. Boom et al, *J. Clinical Microbiol.* 28(3): 495–503 (1990). Several silica based resins are commercially available for use in such methods. For example, a specialized silica-based resin, such as one of the Wizard™ DNA Purification System resins (commercially available from Promega Corporation, Madison, Wis., U.S.A.) is added to the lysate, and is allowed to bind to the nucleic acid of interest such as plasmid DNA. The resin is then loaded onto a column, washed several times using a vacuum or centrifugal force, and the nucleic acid bound to the resin is then eluted from the column with an elution buffer or water.

Although paramagnetic particle and resin methods such as those outlined immediately above are very rapid and selective methods for isolating nucleic acids, neither guarantees the inactivation of nucleases or other harmful proteins at any point during the procedure. In fact, nucleases can even be carried over into the final solution of isolated nucleic acids produced using several such methods. Nuclease carryover can result in severe degradation of nucleic acids isolated with at least the second, resin based, method of purification, particularly in cases where the DNA at issue is isolated from an end A+ bacterial strain. See, e.g. Schoenfeld et al., supra.

As is noted above, proteases have been used to enzymatically degrade proteins in nucleic acid isolation procedures. However, until now, all proteases used to isolate nucleic acids have been inactive in the alkaline pH ranges present in most alkaline lysates. For example, proteinase K is relatively inactive at pH 9 or above, and completely inactive at any pH above pH 10.5, the pH range of a typical alkaline lysate. One the other hand, proteinase K has optimal activity in the approximately neutral pH range (pH 7–8) generally used in restriction digestion or amplification reactions, where residual protease activity in a nucleic acid preparation can degrade enzymes added to the DNA.

Acid proteases, another type of protease whose use in nucleic acid isolation is known, create another host of problems. For example, U.S. Pat. No. 5,386,024 issued to Kacian et al. on Jan. 31, 1995 ("the '024 Patent"), describes a method for "using an acid protease to make available a desired nucleic acid(s) contained in a biological sample". ('024 Patent, claim 1.) The method of the '024 Patent consists of reducing the pH of a biological sample "to a pH below that at which the endogenous nucleases present in the sample are active, and adding a protease active at that low pH which degrades any nuclease that have not been irreversibly inactivated by exposure to low pH, and then inactivating the protease by raising the pH". ('024 Patent, col. 3, lines 5–11). The nucleic acid components of biological samples treated with acid proteases according to the method of the '024 Patent are available for direct use in various detection methods, without further isolation. ('024 Patent, col. 6, lines 39–41). However, Kacian also notes that the low pH used in their acid protease method can cause depurination and chain breakage in DNA ('024 Patent, col. 6, lines 4–6.) Thus, although this last method is well-suited to RNA isolation, its use to isolate intact DNA is limited.

Alkaline proteases (i.e., proteases which are active at a pH of at least 10) have been used in the detergent industry for many years to boost the washing performance of laundry and other commercial detergent formulations. See, for example, Von der Osten et al., *J. Biotechnol.* 28: 55–68 (1993); and Aehle et al., *J. Biotechnol.* 28: 31–40 (1993). Alkaline proteases purified from *Bacillus licheniformis* (*B. licheniformis*) and *Bacillus alcalophilus* (*B. alcalophilus*) are widely used in detergent formulations, being particularly favored for their low toxicity compared to proteases from other organisms, their activity at alkaline pH values, and their compatibility with detergents. Such proteases are produced cheaply and in large quantities for use in the detergent industry. For an example of one of many patented methods used to prepare and to purify alkaline proteases from these last two organisms, see U.S. Pat. No. 5,439,817 issued to Shetty et al. on Aug. 8, 1995.

The present invention addresses the problem of degradation of nucleic acids after release of the nucleic acid and protein components of biological materials during lysis in the presence of an alkaline pH. The present invention also addresses the problem of protein carryover, particularly the carryover of endotoxins and nucleases, in a variety of different nucleic acid isolation procedures. The present invention uses an alkaline protease conveniently to inactivate and degrade nucleases in biological samples, while making the nucleic acids in the sample available for further isolation using any one of a number of different known methods for nucleic acid isolation. Addition of alkaline protease to biological samples according to the method of this invention also leaves the nucleic acids in the sample sufficiently free of inhibitory or degrading enzymes to be used directly for restriction digestion, DNA sequencing, cloning and detection assays, such as hybridization assays or target amplification procedures. The present invention is a quick, simple, and relatively non-hazardous method of removing deleterious proteins from solution, and ensuring that intact and usable nucleic acids are recovered when further nucleic acid isolation is desired. The method of this invention also offers a rapid and efficient means for digesting proteins such as nucleases, which can inhibit or damage nucleic acids, limiting or even completely destroying the usefulness of the nucleic acids so isolated.

The present invention also addresses the need for methods of treating solutions of nucleic acids which contain nucleases capable of degrading the nucleic acids. This embodiment of the method of this invention offers a rapid and efficient means for inactivating the nuclease components of such solutions, thereby protecting the nucleic acids contained therein from degradation or damage by the nucleases.

SUMMARY OF THE INVENTION

It has now been found that alkaline protease can be used to improve the quality of nucleic acids isolated from biological material by digesting harmful proteins such as nucleases in the alkaline pH range typically used in alkaline lysis steps of known nucleic acid isolation procedures. It has also been found that alkaline protease can also be used to treat a solution of nucleic acids to protect the nucleic acids from degradation or damage by nucleases present in the solution. Kits have also been developed for use in isolating nucleic acid material, using alkaline protease. The principal features of these principal embodiments of the present invention are summarized below.

One embodiment of the present invention is a method for treating a nucleic acid solution with an alkaline protease, the solution comprising a nucleic acid material and proteins, the method comprising:

(a) adjusting the pH of the nucleic acid solution to an alkaline pH, thereby forming an alkaline solution;

(b) incubating the alkaline solution in the presence of the alkaline protease, until the proteins are substantially inactivated; and (c) lowering the pH of the solution sufficiently to reduce protease activity.

Another embodiment of the present invention is a method for isolating nucleic acid material from a biological sample comprising protein material and nucleic acid material, the method comprising:

(a) suspending the biological sample in a solution;

(b) adjusting the pH of the solution to an alkaline pH by adding an alkaline lysis solution, thereby forming an alkaline lysate solution;

(c) incubating the alkaline lysate solution in the presence of an alkaline protease, until proteins capable of degrading the nucleic acid material are substantially inactivated; and (d) lowering the pH of the alkaline lysate solution sufficiently to reduce protease activity.

Yet another embodiment of the present invention is a kit for isolating a nucleic acid material, which kit comprises, in separate containers:

(a) an aliquot of an alkaline protease, wherein the alkaline protease is capable of inactivating proteins capable of degrading the nucleic acid material at an alkaline pH; and (b) a resin matrix capable of reversibly binding the nucleic acid material.

The term "incubating" as used herein should be broadly construed to mean maintaining a solution for a sufficient time and at a temperature, whether below, at, or above room temperature, at which a particular enzyme of interest actively digests a particular substrate in the solution. More specifically, the methods of this invention are carried out at a temperature wherein the alkaline protease digests proteins in the solution.

Except where otherwise provided, the term "resin matrix" as used herein should be broadly construed to mean solid resin particles capable of reversibly binding the nucleic acid of interest, wherein the resin particles are in the form of a slurry of particles in a solution, in the form of particles packed in a column, or in the form of particles embedded into a filter or membrane.

DETAILED DESCRIPTION OF THE INVENTION

Figure 1:
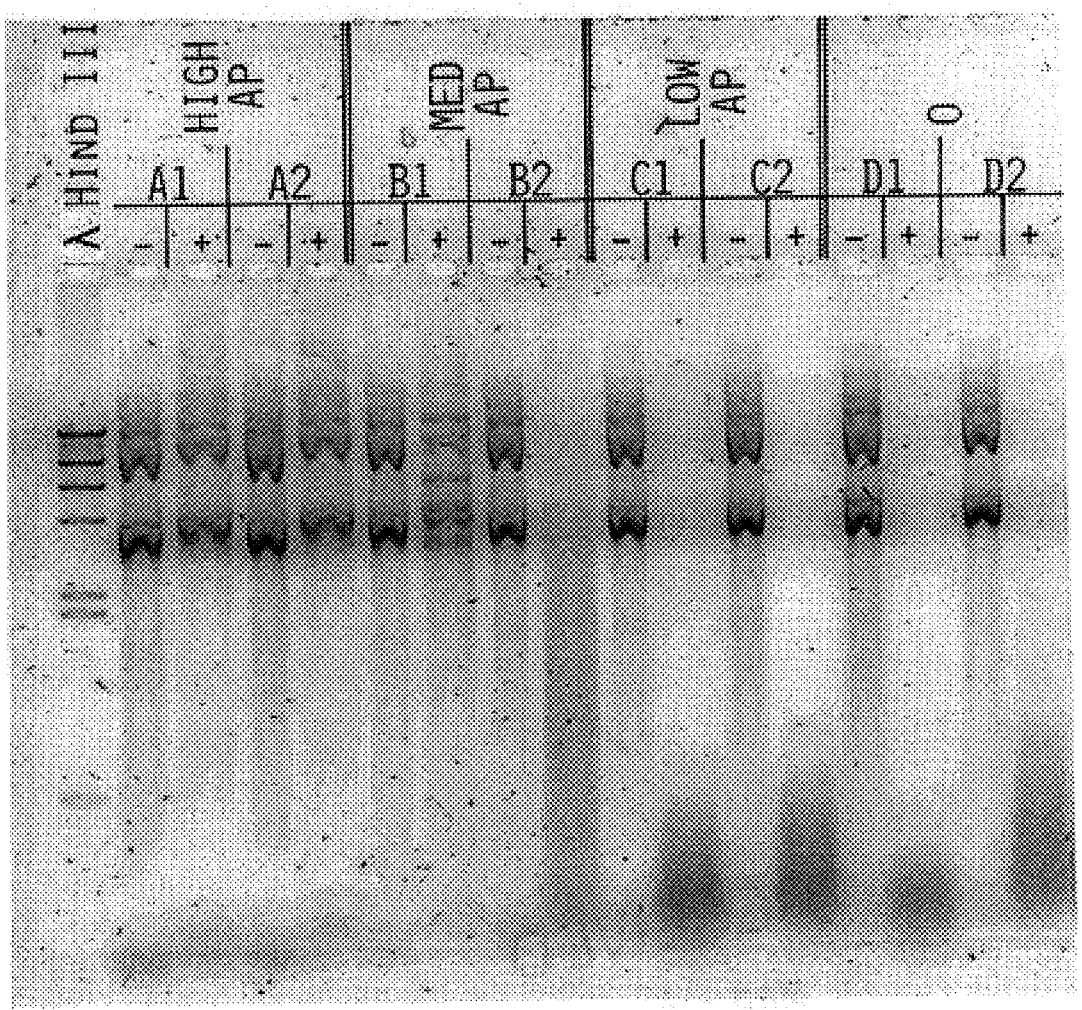
FIG. 1 is a reproduction of an electronic scan of an agarose electrophoresis gel containing fractionated samples of plasmid pGEM®-3Zf(+)DNA isolated from *E. coli* LE392 bacteria (end A+) using decreasing amounts of alkaline protease (samples A1–, A2–, B1–, B2–, C1–, C2–, D1–, D2–), and subsequently incubated overnight at 37° C. in core buffer containing a magnesium salt to detect residual nucleases (samples A1+, A2+, B1+, B2+, C1+, C2+, D1+, D2+).

The present invention, in one aspect, is a method of isolating nucleic acid material from a biological sample, using an alkaline protease wherein the biological sample comprises protein material and nucleic acid material, as described in the general description of the invention, above. In another aspect, the present invention is a method of treating a nucleic acid solution with an alkaline protease, the solution comprising a nucleic acid material and nucleases, as described in the general description of the invention, above.

Preferably, an alkaline protease is chosen for use in either or both of the methods of this invention, which catalyzes the digestion of macromolecules (e.g., proteins) in the sample that may interfere with the intended use of the sample or may degrade nucleic acids isolated from the sample. It is also preferred to choose alkaline proteases which help make available the desired nucleic acids by aiding in the lysis or disgradation of microorganism cell walls, virus particles, ribosomes, and/or other structures containing the desired nucleic acids in the sample. Solubilization of these structures and release of the nucleic acids is preferably effected by including a detergent in the alkaline lysis solution or alkaline solution of nucleic acids in order to denature substrate proteins in the solution, thereby increasing their susceptibility to protease digestion. The alkaline protease and detergent, together in the most preferred aspect of the alkaline lysis solution used in the present methods, ensure that structures containing the nucleic acid material are solubilized. The alkaline protease in the lysate solution also ensures that at least some of the proteins released through the solubilization, particularly nucleases which can degrade the nucleic acid of interest, are enzymatically inactivated.

The alkaline protease selected for use in the method of this invention must be active in digesting proteins at an alkaline pH (i.e., a pH of at least 7.0), preferably at a pH of at least 9, more preferably at a pH of at least pH 10. The alkaline protease selected also must be active in digesting and inactivating nucleases. The alkaline protease selected also preferably digests other unwanted proteins besides nucleases, such as endotoxins, and it even more preferably digests other unwanted components.

The preferred alkaline protease used in both methods of the present invention is isolated from one of the strains of Bacillus bacteria known to produce an alkaline protease active at a pH of at or above 9, preferably an alkaline protease purified from *B. licheniformis* or *B. alcalophilus*, but most preferably an alkaline protease obtained from *B. licheniformis*. The preferred alkaline protease is available from several different commercial sources, a preferred source being Valley Research, Inc. in South Bend, Ind. This protease is particularly favored because of its high efficiency at digesting proteins at the pH typically used to lyse biological samples in prior art alkaline lysis methods (i.e. at a pH of at or above 10). *B. licheniformis* also is favored for its commercial availability, and for its low toxicity compared to other organic solvents (such as phenol) or other proteases (such as proteinase K), both of which are currently used to inactivate deleterious proteins during or immediately after lysis. See, e.g. U.S. Pat. No. 4,843,155 issued to Chomczynski on Jun. 27, 1989.

Step (a), of the method of isolating nucleic acids of this invention, and the first step in a preferred aspect of the method of treating a nucleic acid solution of this invention comprises suspending a biological sample in a solution. Preferably, a suspension solution is used, as is described in greater detail below. The biological sample used can be any of a number of different types or mixtures of biological material, including bacterial cells, viral particles, plant tissue, or animal tissue.

The method used to suspend a given biological sample in solution will depend upon its nature. For example, a pellet of bacterial cells or of animal blood can generally be suspended by adding a solution and mixing gently with a pipette or by inversion. However, many forms of plant, animal, or fungal tissue require more vigorous treatment before being suspended, such as freezing and pulverizing, or by homogenization with a blender or other mechanical mixing device.

The use of a suspension solution, as noted above, is preferred. A suspension solution of this invention is preferably an aqueous solution, and more preferably is an aqueous solution comprising a buffer, even more preferably further comprising a Tris-HCl buffer, yet more preferably further comprising a Tris-HCl pH 7.5 buffer. A suspension solution of this invention also preferably comprises a chelating agent, e.g., ethylenediamine tetra-acetic acid (EDTA). When the nucleic acid material to be isolated is a DNA material, the suspension solution preferably additionally comprises an RNase enzyme which is active at the pH of the suspension solution, and more preferably which does not degrade or inhibit the DNA material of interest. A particularly preferred RNase enzyme is RNase A.

In another step of a preferred aspect of the method of this invention, the pH of the suspension solution is adjusted to an alkaline pH by adding an alkaline lysis solution. The alkaline lysis solution comprises a base, preferably a base which is strong enough to raise the pH of the solution to a level wherein the alkaline protease is highly active, but which is not so strong as to damage the nucleic acid material to be isolated. The preferred base is an aqueous solution of sodium hydroxide. The alkaline lysis solution preferably further comprises a detergent, preferably an anionic detergent, and more preferably sodium N-lauryl sulfate (SDS). The detergent component of the lysis solution disrupts the lipid components of biological materials, such as the cell walls of plant or fungus cells, or the membranes of bacteria, or animal cells, thereby making any material such as proteins or protein-nucleic acid complexes contained within those cell walls or membranes available for digestion by an alkaline protease. In the case of tougher cell walls such as the walls of many plant or fungal cells, it is contemplated herein that a base and/or detergent alone or together may not sufficiently disrupt the cell walls to release the nucleic acid material. In such cases, predigestion of the cells with, e.g., an anionic detergent and proteinase K, prior to addition of the alkaline lysis solution may be necessary to ensure adequate lysis.

In another embodiment of the method of this invention, the pH of the nucleic acid solution is preferably adjusted prior to treatment with alkaline protease, using an alkaline lysis solution of the same composition described herein above.

The alkaline protease must be present in solution for proteins to be digested in the incubation step of the method. However, the alkaline protease can be added to the solution at any earlier step of the method, as it does not become highly active until the pH is raised to at or above pH 9. The alkaline protease is preferably added to the solution after the pH is raised, particularly in cases wherein the method is used to isolate a DNA material and wherein an RNase is present in or added to the solution of suspended biological material. The amount of alkaline protease needed to substantially inactivate degradative proteins in the lysate, e.g., nucleases, can be determined using a simple protection assay, such as the assay described in Example 6.

The incubating step of either the treatment or isolation methods of this invention is preferably carried out by incubating the alkaline nucleic acid or alkaline lysate solution at a temperature between 0° C. and 67° C. until proteins capable of degrading the nucleic acid material are substantially inactivated. The amount of time needed to ensure substantial inactivation of such proteins will vary, depending upon the incubation temperature chosen. Lower temperatures slow enzymatic activity, while higher temperatures tend to enhance it up to the point at which the temperature of incubation is so high that at least some of the enzyme is inactivated. The incubation temperature is more preferably below at least 45° C., even more preferably below at least 37° C., and most preferably at about room temperature (25° C.).

The alkaline nucleic acid or lysate solution is incubated in the presence of the alkaline protease at a high enough temperature that the protease is active in digesting the protein material from the sample, but not so high a temperature that the nucleic acid material is damaged. It is contemplated that different alkaline protease species will be active at different temperatures. The most preferred alkaline protease used in the method of this invention is active at room temperature, and the incubation step is most preferably carried out at about that temperature for at least about one minute, and most preferably for at least about five minutes.

The methods of this invention can be used to isolate any nucleic acid material. However, it is most preferably used to isolate DNA. RNA tends to degrade in solutions maintained at a high pH for any length of time. Therefore, when RNA is isolated according to the methods of this invention, it must be done at a pH low enough that RNA is not degraded but at a pH which is high enough for the alkaline protease to be active. DNA can survive intact at very high pH levels. However, if left at a high pH level for a long time, DNA tends to denature and to be damaged. Consequently, in practicing the method of this invention, the lysis solution should not be maintained at the pH at which the alkaline protease is active (the "high pH") any longer than is necessary to permit the alkaline protease to digest all or substantially all of the nucleases present in the solution. The lysis solution is preferably maintained at that high pH for no longer than 30 minutes, more preferably no longer than 15 minutes, even more preferably no longer than 10 minutes, and most preferably no longer than 5 minutes.

In a further step of the methods of this invention, the pH of the alkaline nucleic acid or lysate solution is lowered, after incubating with alkaline protease, to a pH sufficient to render the protease less active. Generally speaking, it is contemplated that a protease present in the solution will be rendered less active by reducing the pH of the solution at least 1 pH unit. In a preferred practice, the alkaline protease is rendered inactive (as contrasted with merely reducing its activity), preferably by lowering the pH to below pH 8, more preferably by lowering the pH of the mixture to at least as low as a neutral pH, and most preferably by lowering the pH to at or about a neutral pH. With some alkaline proteases, lowering the pH to the preferred pH range is sufficient to completely stop further proteolytic digestion in the mixture, and it may even irreversibly denature and inactivate the enzyme. With other alkaline proteases, it may be necessary to resort to heating the sample to achieve complete inactivation of the protease. The most preferred alkaline protease, an alkaline protease isolated from *B. licheniformis*, can be completely inactivated by heating a solution containing the protease at 67° C. for as little as 5 minutes. By the time the protein components of the lysate are digested with the alkaline protease, and the pH lowered, the nucleic acids will survive intact a heating procedure at the lower pH.

Once the alkaline protease activity is reduced or it is rendered inactive, the nucleic acids remaining in solution can be used directly in various applications or isolated from other materials in the mixture by performing additional isolation steps well known to one skilled in this art.

If the pH of the alkaline lysate solution is lowered to about a neutral pH, a precipitate will usually form. When the biological sample lysed is cellular material such as bacterial cells, the precipitate formed at this step of the method is composed, primarily, of proteins, polysaccharides, lipids, and genomic DNA. If not removed, this precipitate can interfere with some uses of the nucleic acid material in subsequent procedures. Consequently, in a preferred embodiment of the method of this invention, any precipitate formed during the alkaline protease activity reduction/inactivation step is removed to form a cleared lysate. The precipitate can be removed by filtration or by centrifugation, but is most preferably removed by centrifugation. When placed in a centrifuge container and exposed to centrifugal force, the precipitate forms a pellet on the bottom and sides of the container, so that the cleared lysate can be removed by decantation or pipetting. The nucleic acid material in the cleared lysate then can be used directly, or can be further isolated using any of a number of well-known isolation techniques.

In a preferred practice of this invention, nucleic acid material in the cleared lysate (above) is isolated from other biological material in the solution using further isolation steps. While three such techniques, suitable for use with this invention, are described below, it is to be understood that the present invention is not to be limited to any of these techniques.

A first such suitable additional isolation technique uses precipitation of the nucleic acids with alcohols. Alcohol is added to the cleared lysate causing the nucleic acids to precipitate. The nucleic acid is then collected by centrifugation and the supernatant is removed. The DNA precipitate is then redissolved in a suitable aqueous buffer. Bimboim, H. C. 1983, *Methods in Enzymology*, Vol. 100, pp. 243–255; Bimboim, H. C. and Doly, J. 1979, *Nucleic Acids Res.*, Vol. 7, pp. 1515–1523.

A second additional isolation technique suitable for use in the method of this invention uses magnetic particles to isolate the nucleic acid material of interest. In this method, the nucleic acid material is reversibly bound to a magnetic particle, and magnetic force is used to separate the bound nucleic acid from other biological materials in the solution.

The nucleic acid material is then released from the particle into a second solution. The magnetic particle is preferably a paramagnetic particle, and more preferably, a paramagnetic particle which has been tested for use in isolating nucleic acids. Streptavidin MagneSphere® Paramagnetic Particles commercially available from Promega Corporation, Madison, Wis., are particularly preferred paramagnetic particles. A preferred method of additionally isolating nucleic acids using magnetic particles is described in PCT Publication No. WO 96/09308, the teaching of which is incorporated herein by reference.

A third, and most preferred additional isolation technique uses a resin matrix to reversibly bind the nucleic acid material. The cleared lysate is added to a suitable resin matrix in the presence of a sufficient amount of a chaotropic agent to cause the nucleic acid to bind to the resin component of the matrix. Once bound to the resin, the nucleic acid/resin complex is preferably washed at least once, using an external force such as centriftigation or a vacuum to remove the wash solution. The nucleic acid material is then released from the resin matrix using an elution buffer or water.

The preferred resin for use in the method described above is silica based particles. Suitable silica resin material for reversibly binding nucleic acids includes glass powder and diatomaceous earth. See, e.g. U.S. Pat. No. 5,075,430 issued to Little on Dec. 24, 1991; or U.S. Pat. No. 5,155,018 issued to Gillespie et al. on Oct. 13, 1992, the teachings of which are incorporated by reference herein. The resin used in the preferred isolation methods of this invention consists of solid particles of silica material in a matrix. Any one of a number of different resin matrix formats are contemplated for use in the nucleic acid isolation methods of this invention, including silica based resin particles in the form of a liquid/particle slurry, in the form of a packed column, or in the form of a filter or membrane. A preferred resin matrix is one of the resin slurries or packed columns commercially available from Promega Corporation, Madison, Wis., U.S.A. for use with its Wizard™ DNA Purification Systems. A more preferred resin matrix is one of the embedded filter materials commercially available from Ansys Corporation, Irvine, Calif. Particularly preferred is the SPEC™ silica disc material available from Ansys. Other preferred commercially available resin matrices are sold by Qiagen Corporation with its own DNA purification systems. Suitable silica based resin compositions for use in the present method are also described in PCT Publication No. WO 95/06652, incorporated herein by reference.

Those skilled in the art of nucleic acid purification will recognize that the methods of this invention could also be used to improve the quality of any nucleic acid material, including RNA isolated from a variety of biological samples. One of the standard methods of RNA extraction involves disruption of tissue in the presence of high concentration of chaotropic salts such as guanidine thiocyanate followed by organic extraction with a mixture of phenol and chloroform. In this extraction the RNA partitions into the aqueous phase and contaminants such as DNA and denatured and inactivated proteins are partitioned into the organic phase and interphase layers, respectively. A single extraction however, will not effectively remove or inactivate all of the contaminating nuclease and thus requires multiple extractions. Each extraction however, results in reduced recovery of RNA from the sample. The elimination of nucleases that degrade RNA from the sample must be quantitative. These enzymes are known to be very stable and can renature to their active form during long term storage of the RNA. This can result in a slow degradation of the RNA during storage of the sample. It should be further recognized that different starting material will contain varying amounts of ribonuclease activity making it difficult to standardize the extraction procedure for all starting materials.

Under the appropriate conditions RNA can be reversibly bound and eluted from a silica particle. It is envisioned that the aqueous phase from an organic extraction could be treated with an alkaline protease followed by purification using a silica particle. In order to carry out such treatment isolation steps, the aqueous phase would first be adjusted to a pH that would be sufficient for an alkaline protease to be active (pH range of 7–9) but not allow for the alkaline hydrolysis of the RNA sample. After an incubation time sufficient to allow for the degradation and inactivation of residual ribonuclease the aqueous phase would be adjusted to the appropriate concentration of chaotrope to allow for the binding of the RNA to the silica, washed as described previously for the DNA and then the RNA eluted in a buffer of low ionic strength. This procedure would eliminate the need for multiple extractions and improve the yield and purity of the RNA.

The present invention is further illustrated by the following examples. These examples are intended to be illustrative of the invention and should not be used to limit or restrict its scope.

EXAMPLES

The nine examples below either illustrate one of the preferred embodiments of the method of isolating DNA of this invention, or they analyze the isolated products of one or more of the embodiments of that preferred form of the method illustrated below. Except where otherwise provided, all of the procedures used to isolate plasmid DNA in the examples below used a resin matrix of silica particles embedded in a membrane, specifically a pair of SPEC™ silica filter discs seated in the bottom of a spin column small enough to fit inside of a 2 ml microfuge tube. This specific configuration of silica filter disks and spin column is referred to herein below as a "spin basket" or as a "basket".

The first four examples below illustrate the effect of isolating a specific nucleic acid material, plasmid DNA, from two different end A+ strains of *E. coli* bacteria, LE392 and Y1090, using varying amounts of alkaline protease. All examples herein used spin baskets, as described above, to additionally isolate the nucleic acid material of interest after an initial alkaline lysis step, done with or without alkaline protease. Except where indicated below, all the solutions used in these first four examples were components of Wizard™ Plus DNA Purification Systems kits obtained from Promega Corporation. The amount of protection accorded plasmid DNA isolated in these first examples was found to increase with the amount of alkaline protease used to digest nucleases in the alkaline lysis step of the specific isolation procedure used herein.

Alkaline protease residue was analyzed in Example 5 in samples of plasmid DNA isolated using excess amounts of alkaline protease in the alkaline lysis step. The amounts of residual protease found were minuscule compared to the amount added, with only about 1/10,000th of the amount added found carried over into the final solution of isolated plasmid DNA.

Example 6 describes the alkaline protease activity assays used in the next example. In the next example, Example 7, dilute alkaline protease solutions, whether solutions of diluted stock solutions of proteases or solutions of protease contaminated solutions of isolated plasmid DNA, were tested to discover whether the proteases in the solutions could be inactivated by heating at 67° C. Heating at that temperature for only five minutes was shown to inactivate the alkaline proteases in both types of solutions, the diluted stock or contaminated plasmid DNA solutions.

The last two DNA isolation and analysis examples describe assays of the identity and functional purity of plasmid DNA isolated using alkaline protease, according to the method of Examples 1 and 2. In the first of these last two examples, Example 8, samples of isolated plasmid DNA were sequenced using an automated fluorescent sequencing, a sequencing technique known for its sensitivity to contaminants in a sample. This assay demonstrated that the sequence of the isolated plasmid DNA matches the sequence of the plasmid DNA used to transform the bacteria cells from which the DNA was isolated, thereby confirming the identity of the isolated DNA. The high quality of the resulting sequencing data further demonstrated the functional purity of the isolated DNA.

The final such example, Example 9, demonstrated that isolated plasmid DNA containing a gene of interest can be transfected into tissue culture cells and the gene successfully expressed therein. In this example, a plasmid containing a luciferase gene was transfected into two different tissue culture cell lines, one obtained from cancerous human tissue and the other from a hamster ovary. Only cells transfected with the plasmid could produce luciferase, as luciferase is not a protein naturally produced by either cell line tested. Luciferase is the principal enzyme known for causing firefly tails to glow. The luciferase gene is a popular reporter gene, as its expression in most organisms can be readily detected and quantified using a luminometer. Luciferase gene expression was detected in both sets of tissue culture cells transfected with isolated plasmid DNA, indicating that the DNA isolated according to the method of this invention is sufficiently intact and free of contaminants to successfully transfect tissue culture cells.

Example 10 illustrates an embodiment of the method of the present invention, in which the method is used to treat a nucleic acid solution containing a nucleic acid material and proteins.

Example 11 describes the use of the method of this invention to produce and treat an aqueous solution of RNA extracted from a biological material.

Example 12 illustrates the use of a silica resin matrix to isolate RNA from the aqueous solution of RNA produced and treated in Example 11.

Detailed descriptions of all the examples are provided below.

Example 1
Production of a Cleared Lysate

The particular plasmid in this example, plasmid PGEM® 3Zf(+), was isolated from end A+ strains of *E. coli* bacteria. Two such strains, Y1090 and LE392 were transformed with this plasmid, and grown up separately in an overnight culture of 2×YT+1% glucose+ampicillin, a rich complete media which increases the production of endonuclease compared to standard media, such as Luria Broth (LB) or a minimal media. The bacteria cells were then harvested by centrifugation, resuspended in suspension solution at a ratio of 0.25 ml of suspension solution to the equivalent of 10 ml culture, and 250 µl aliquotted into each of several centrifuge tubes.

The resuspended cells formed a uniformly cloudy solution in each tube. The suspension solution composition was: 50 mM Tris-HCl, pH 7.5; 10 mM EDTA; and 100 μg/ml RNase A. The number of aliquots of resuspended cells varied, depending on the number of tests to be run in each example below.

250 μl of an alkaline cell lysis solution was added to the suspended cells, and mixed with the cells by inversion, the solution becoming clear (indicating the formation of a lysate) within 1–5 minutes. The composition of the lysis solution added was 0.2M NaOH and 1% SDS. The resulting lysate had a pH of about 10.

10 μl of an alkaline protease solution or 10 μl of alkaline protease dilution buffer was added to each of the lysate samples. The composition of the dilution buffer was 25% 1, 2 propanediol, 3.2% sodium borate, pH 6.3. Differing concentrations of alkaline protease were used for the alkaline protease solution added at this stage of the procedure. The concentrations used are indicated in subsequent examples herein below. The protease solutions were prepared by diluting a stock solution of an alkaline protease isolated from *B. licheniformis* in the dilution buffer described above. The alkaline protease used in this and in subsequent examples below was obtained from Valley Research, South Bend, Ind., U.S.A. (Product Number APL660). Once the 10 μl of alkaline protease or dilution buffer was added, the lysate was mixed by inversion; and the resulting mixture was incubated for 5 minutes at about room temperature.

The pH of the mixture was lowered by adding 350 μl of an acidic neutralizing solution to each tube of mixture, and by mixing by inversion. A precipitate was formed making the mixture cloudy in appearance. The composition of the acidic neutralizing solution was: 4M guanidine hydrochloride; 0.759M potassium acetate; 1.62M glacial acetic acid, pH 4.2. The cloudy lysate mixture was centrifuged at 14,000×g in a microcentrifuge for 10 minutes at room temperature forming a cleared lysate with a pellet of precipitate at the bottom and sides of the tube.

Example 2
Isolation of Plasmid DNA from a Cleared Lysate

One spin basket was placed in a 2 ml collection tube for each sample to be tested. The cleared lysate was transferred to the spin basket using a pipettor. The basket was then centrifuged at 14,000×g in a microfuge for 1 minute at room temperature forcing the cleared lysate to pass through the silica impregnated membrane component of the spin basket. The basket was then removed, the solution collected in the collection tube discarded, and the basket reinserted into the same collection tube.

The basket contents were washed twice with a wash solution, the wash solution consisting of 0.01M NaCl, 0.01M Tris-HCl (pH 7.5), and 80% ethanol. In the first wash step, 750 μl of wash solution was added to the basket, and the basket/tube combination centrifuged at 14,000×g in a microcentrifuge for 1 minute at room temperature. The solution collected in the collection tube was discarded, as before. In the second wash step, the same procedure was followed using 250 μl of the wash solution.

The basket was then transferred to a clean 1.5 ml microcentrifuge tube, using care so as not to transfer any of the wash solution with the basket. The plasmid DNA was eluted from the resin in the basket by adding 100 μl of nuclease-free water and centrifuging the sample at 14,000×g in a microcentrifuge for 1 minute at room temperature. The basket assembly was then removed from the tube and discarded. The tube of isolated plasmid DNA was capped and placed at +4° C. until used in the tests described in the examples, below.

Example 3
Assaying Alkaline Protease Levels that Protect Plasmid DNA

In this example, varying amounts of alkaline protease were used in the alkaline lysis step of the cleared lysate production procedure of Example 1. The isolation procedure of Example 2 was then used to isolate plasmid DNA from the cleared lysate. The resulting solutions of isolated nucleic acid material were tested to determine: (1) whether the plasmid DNA in the solution was significantly nicked or degraded, and (2) whether the solution contained nucleases which would nick or degrade the plasmid DNA after overnight incubation at 37° C. in 1× core buffer.

The core buffer solution used in this example was designed to facilitate enzyme activity including the activity of nucleases, such as endonuclease I. The composition of the 1× core buffer used was as follows: 25 mM Tris-acetate pH 7.8 (at 25° C.), 100 mM potassium acetate, 10 mM magnesium acetate, 1 mM DTT. The 10× core used to make this 1× solution was obtained from Promega Corporation, Madison, Wis., U.S.A.

Gel electrophoresis was used to determine whether the plasmid DNA from each of the two tests described above was degraded or nicked. Below is a detailed description of the tests performed in this example.

Plasmid pGEM® 3Zf(+) was isolated from *E. coli* strain LE392 (end A+) in duplicate for preparations which used 10 μl protease solutions which contained: 3.7 mg protease/ml (Samples A1 and A2); 470 μg protease/ml (Samples B1 and B2); 58.5 μg protease/ml (Samples C1 and C2); and; 0 μg protease/ml (i.e., dilution buffer control) (Samples D1 and D2). The DNA was isolated according to the procedure described in Examples 1 and 2.

Detection of endonuclease activity in the final DNA preparations was performed by aliquotting 15 μl of DNA into each of two separate containers to use as duplicate samples, and adding 2 μl of 10× core buffer to one of the duplicate samples. The samples were then incubated at 37° C. overnight and followed by fractionation on a 1% agarose gel in Tris-acetate-EDTA (TAE) electrophoresis buffer, containing 0.5 mM iodopropyl thiazole orange (IPTO), a fluorescent nucleic acid staining dye. Following fractionation, the gel was then scanned using a Fluorimager (Molecular Dynamics) to visualize the DNA bands. FIG. 1 is a copy of the image produced from the scan of this gel.

The presence of intact plasmid DNA on an electrophoresis gel is indicated by a band of supercoiled DNA which migrates faster than the dimer, nicked monomer, or nicked dimer bands frequently found in plasmid DNA preps. Additional bands can sometimes also be found in plasmid DNA preps, migrating slower than any of the dimer or monomer bands, corresponding to multimers and nicked multimers. The gel picture in FIG. 1 is positioned such that the fastest migrating bands are nearer to the bottom of the page than the slower migrating bands. Degradation of plasmid DNA, in any of the forms described above, is indicated on such a gel image by the disappearance or reduction in intensity of one or more of these bands compared to a sample of intact DNA, and/or by the appearance of smears below the principal bands, indicating the presence of lower molecular weight degraded plasmid DNA.

FIG. 1 shows the results of the duplicate tests run on the samples of plasmid DNA isolated as described above (Samples A1, A2, B1, B2, C1, C2, D1, and D2). Specifically, FIG. 1 is a copy of the image produced from scanning the electrophoresis gel used to fractionate the duplicate samples (A1, A2, etc.) wherein no core buffer was added (indicated by a "−" symbol after the sample number), and side-by-side with a sample incubated with core buffer (indicated by a "+" symbol after the sample number).

Examination of FIG. 1 demonstrates that intact plasmid DNA was recovered from each of the aliquots of culture processed (i.e. the samples indicated by a "−" symbol in the Figure). FIG. 1 also demonstrates that the plasmid DNA was completely degraded in the duplicate samples incubated in the presence of core buffer which were not treated with protease (Samples D1+ and D2+). Incubated samples treated with the largest amount of protease (Samples A1+ and A2+) during isolation showed no evidence of degradation, with those treated with the intermediate amount of protease (Samples B1+ and B2+) showing a significant amount of degradation, and with those treated with the smallest amount of protease (Samples C1+ and C2+) being completely degraded.

This example demonstrates that alkaline protease can be used to eliminate the degradation of isolated plasmid DNA if it is added to the alkaline lysate during isolation of the DNA. It further demonstrates that the amount of protease added must be determined empirically for each protease using a protection assay method such as described above. Once such a determination is made, and levels of protease which protect the DNA are determined, there is no need to repeat the experiment as long as the activity of the protease and the purification procedure are unchanged. This example demonstrates that optimal protection of plasmid DNA can be obtained using the isolation method described above, if a solution of at least about 10 μl of at least about 3.7 mg/ml of alkaline protease is added at the alkaline lysis step.

Example 4
Alkaline Protease Protection Assays in Different *E. coli* Strains

Plasmid pGEM® 3Zf(+) was isolated from a different end A+ strain of *E. coli*, Y1090, using the same procedure and same alkaline protease levels as in Example 3, and testing for endonuclease contamination as above.

Figure 2:
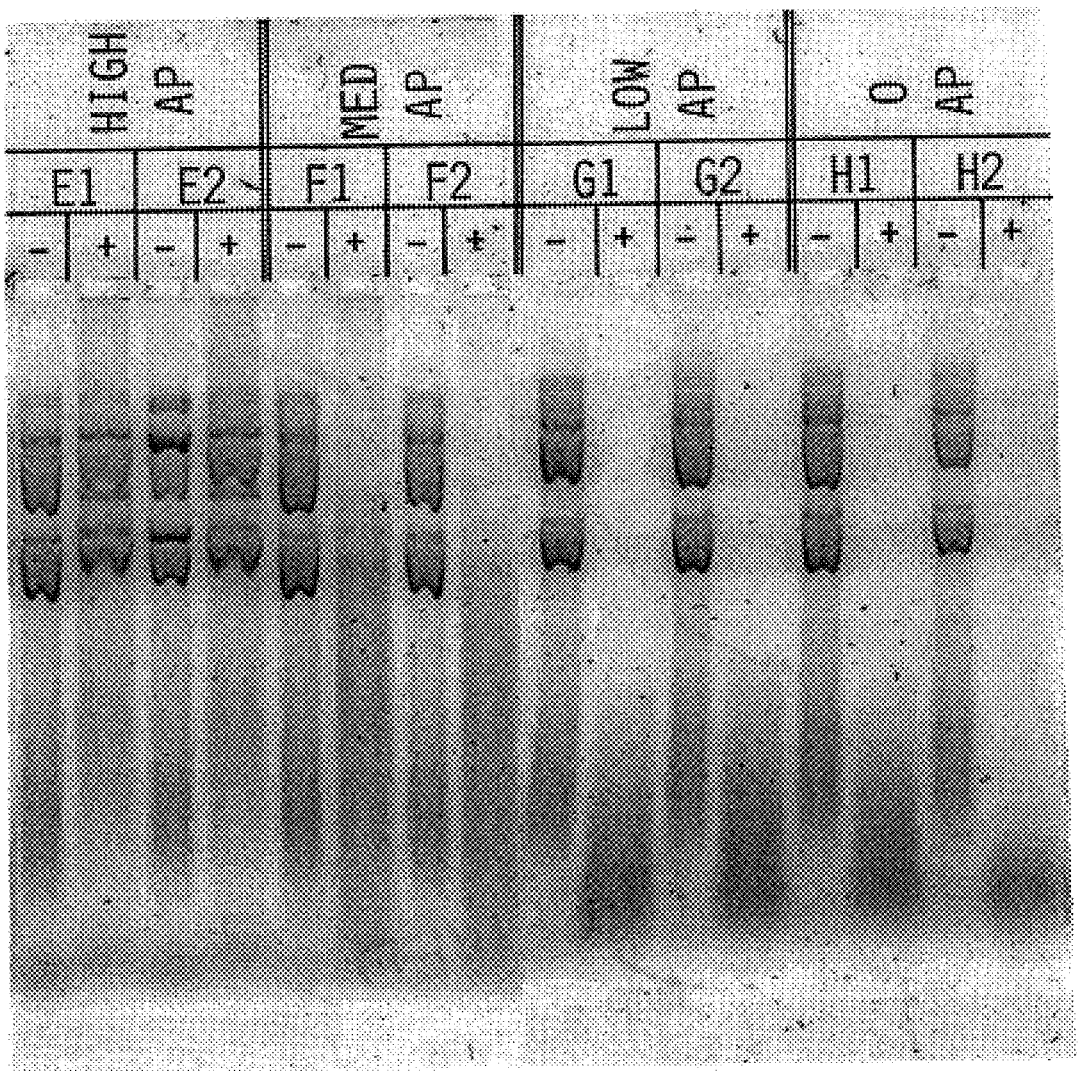
FIG. 2 is a reproduction of an electronic scan of an agarose electrophoresis gel containing fractionated samples of plasmid pGEM®-3Zf(+) DNA isolated from *E. coli* Y1090 bacteria (end A+), using the same concentrations of alkaline protease and test conditions described for FIG. 1, above.

The results of this assay are apparent from FIG. 2 which shows an electrophoresis gel produced, run and scanned as in Example 3. The samples were labeled with the same "+"/"−" nomenclature used to indicate incubation with or without core buffer or incubation with water, respectively as in FIG. 1. A sample numbering system similar to that of FIG. 1 was also used, with Samples E1 and E2 indicating the addition of 10 μl of an alkaline protease solution containing 3.7 mg protease/ml, with Samples F1 and F2 indicatin use of a protease solution with 470 μg protease/ml, with Samples G1 and G2 indicating use of a protease solution with 58.5 μg protease/ml, and with H1 and H2 indicating no addition of alkaline protease (i.e. 0 μg protease/mi).

As in Example 3, intact plasmid DNA was purified from each sample tested. Also, as in Example 3, the plasmid DNA was completely degraded in the samples incubated with core buffer in the water controls where no alkaline protease was added, (H1+ and H2+) and in the samples with the smallest amount of protease added (G1+ and G2+). The plasmid DNA was somewhat protected in the samples with a medium amount of protease added (F1+ and F2+). No degradation was observed in the samples with the largest amount of protease added (E1+ and E2+).

Therefore, this Example indicates that a protease solution containing at least about 3.7 mg protease/mi can be used to protect plasmid DNA isolated according to the procedure of Examples 1 and 2 from degradation by nucleases, particularly when the DNA is isolated from an end A+ strain of bacteria.

Example 5
Assay of Alkaline Protease Carryover in DNA Preparations

In this example, plasmid DNA was isolated from an end A+ strain of *E. coli* using concentrated solutions of alkaline protease in the procedure of Example 1 to produce a cleared lysate, and of Example 2 to isolate the plasmid DNA from the lysate. An excess of alkaline protease was used in the isolation procedure of the two earlier examples in order to determine whether the plasmid solution isolated under such conditions contains active alkaline protease.

Plasmid pGEM® 3Zf(+) was isolated from *E. coli* strain LE392 (end A+) in five replicates for preparations which used 10 μl protease solutions which contained: 15 mg protease/ml, 10 mg protease/ml, or 7.5 mg protease/ml. A fourth triplicate set of samples without addition of alkaline protease, was included as a control. The DNA was isolated using the procedure described in Examples 1 and 2, above.

The amount of alkaline protease in the final DNA solution was determined by adding half of each isolated DNA solution to a reaction mixture which contained a colorimetric substrate for alkaline protease and determining the absorbance of the solution at 410 nm over time. The rate of increase of absorbance at 410 nm was then compared to a calibration curve constructed by measuring the absorbance of solutions of alkaline protease of known composition, containing alkaline protease amounts ranging from 0–25 ng of protease per assay. The rate of absorbance increase in the calibration solutions per amount increase in protease concentration was found to be linear. Therefore, the amount of protease in samples from isolated DNA preparations was extrapolated from the rate of color formation determined for these samples. The Table 1 below gives the level of protease found in the preparations of the ratio of protease found to that added during DNA isolation.

TABLE 1

| Protease Sol'n Concentration | Total Protease Added | Avg. Residual Protease | Ratio of Prot. Residual/Added |
| --- | --- | --- | --- |
| 0 mg/ml | 0 ng | 0 ng | N/A |
| 7.5 mg/ml | 75000 ng | 2.0 ng | 0.0000266 |
| 10 mg/ml | 100000 ng | 4.13 ng | 0.0000413 |
| 15 mg/ml | 150000 ng | 7.75 ng | 0.0000516 |

Only a very small amount of the excessive amounts of added protease, i.e., less than about 0.01%, was found to be carried over into the isolated plasmid DNA solutions produced in this example.

Example 6
Techniques Used to Assay Alkaline Protease Activity

This example describes the method used to assay alkaline protease activity in the examples presented herein. The alkaline protease used in the examples, a protease isolated from *B. licheniformis*, cleaves proteins at hydrophobic residues, cleaving such residues considerably more rapidly than it cleaves protein molecules at hydrophilic or charged residues. This assay takes advantage of the specificity of the enzyme and a commercially available substrate for such proteases to determine the amount of the protease in solution.

This assay is intended to be used to measure the alkaline protease activity of very dilute solutions of the protease. It requires the use of a microtiter plate reader and takes 1–3 hours to perform. The assay is very sensitive, and can measure as little as 1 ng of alkaline protease/ml of solution.

1. Materials 0.5M Tris—HCl pH 9.0 at room temperature 20 mg/ml of Ala-Ala-Phe-p-nitroanilide, Sigma product A-9148 or equivalent dissolved in dimethylformamide 50 mM sodium phosphate pH 5.0 clear flat bottom microtiter plates microtiter plate reader capable of reading absorbance in the 380–410 nm wavelength range 2. Procedure a. Make an assay solution mixture. One ml of the solution is made by adding 10 µl of the dimethylformamide solution to 990 µl of the 0.5 m tris-HCl buffer. Place 200 µl of the assay solution into each well to be monitored. The reagent will be needed for all samples, standards and blanks.

b. Prepare protease standards. The amount of alkaline protease carryover is usually very low, so the standards usually range from about 0 to abut 10 ng/well. The standards are made by diluting a stock solution of alkaline protease into 50 mM sodium phosphate, pH 5.0.

c. Put the samples of DNA preps and standards in the wells and read the plate at 410 nm using a microtiter plate reader.

It is not crucial to start all the assays at the same time. The most effective method for performing the assay is to assemble all of the assays and read the plate very shortly after the last addition. Use the values at the first reading as a zero time point and reread the plate 30–120 minutes later and determine the absorbance difference in the wells.

Example 7
Inactivation of Alkaline Protease Residue in DNA Preparations

There may be some applications where even the small amounts of alkaline protease in the final DNA preparation, such as the amounts observed in Example 5, above, would inhibit the use of the isolated DNA. For such applications, it would be useful to have a simple, rapid method to eliminate the protease activity in the preparation. This Example demonstrates the effectiveness of one such procedure for inactivating residual alkaline protease, i.e., by heating the sample.

In order to determine the minimal time needed to inactivate alkaline protease carried over into an isolated plasmid DNA solution, several of the samples of alkaline protease containing isolated plasmid DNA solutions from Example 5, above, were pooled for further testing. The single sample of pooled material was mixed well, and divided into five new samples for further testing, as is further described below. A second set of five control samples was similarly created by pooling and dividing the dilute stock solutions used in Example 5. The five test and five control samples were heated at 67° C. for different times, with one of each set of samples heated for 0, 3, 5, 7, or 9 minutes. Following the heating, each sample was tested for alkaline protease activity, as described in Example 5, above.

Figure 3:
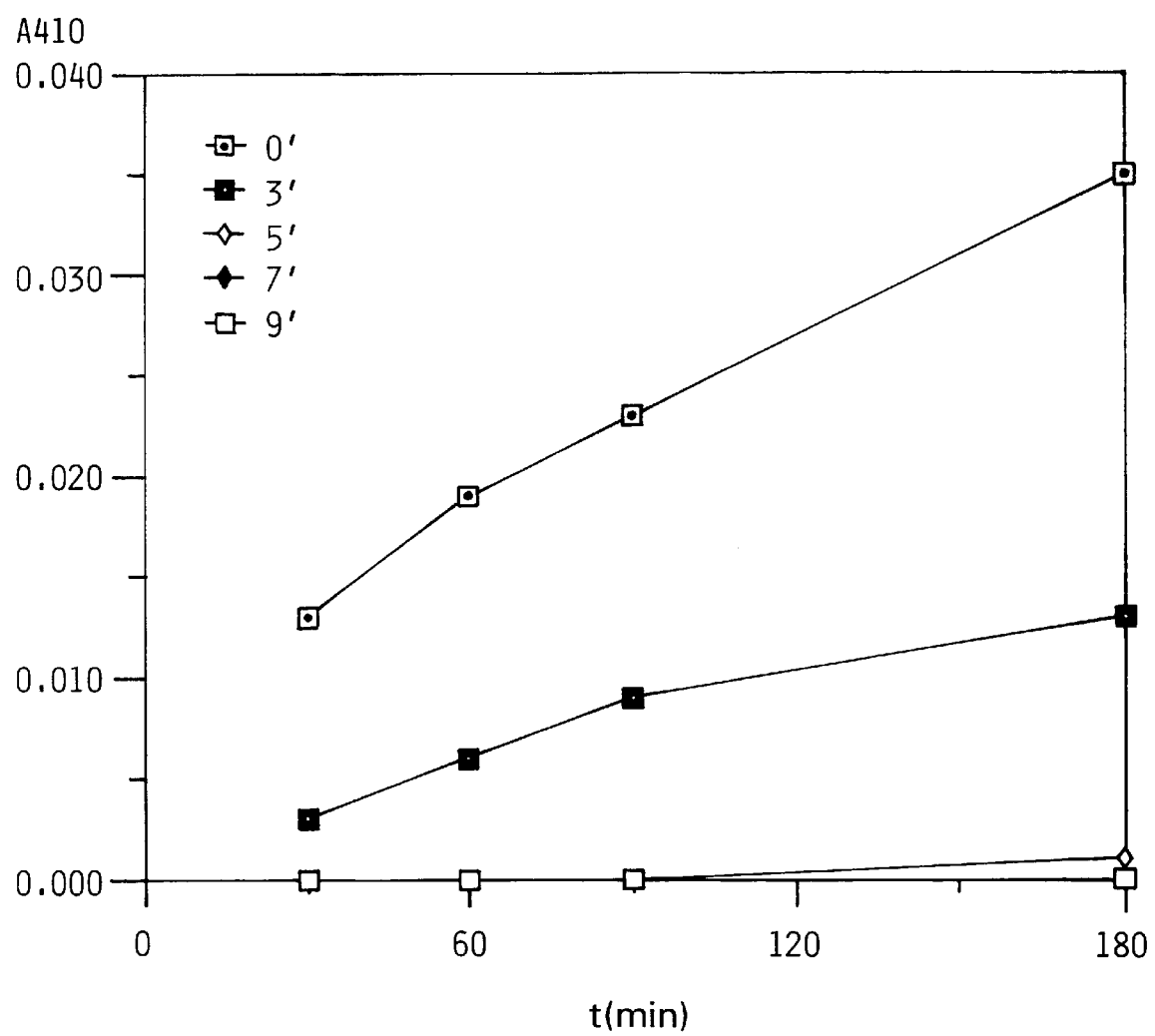
FIG. 3 is a graph of absorbance values measured over time in a protease activity assay of plasmid DNA samples isolated using the method of this invention, following heating at 67° C. for 0, 3, 5, 7 or 9 minutes.
Figure 4:
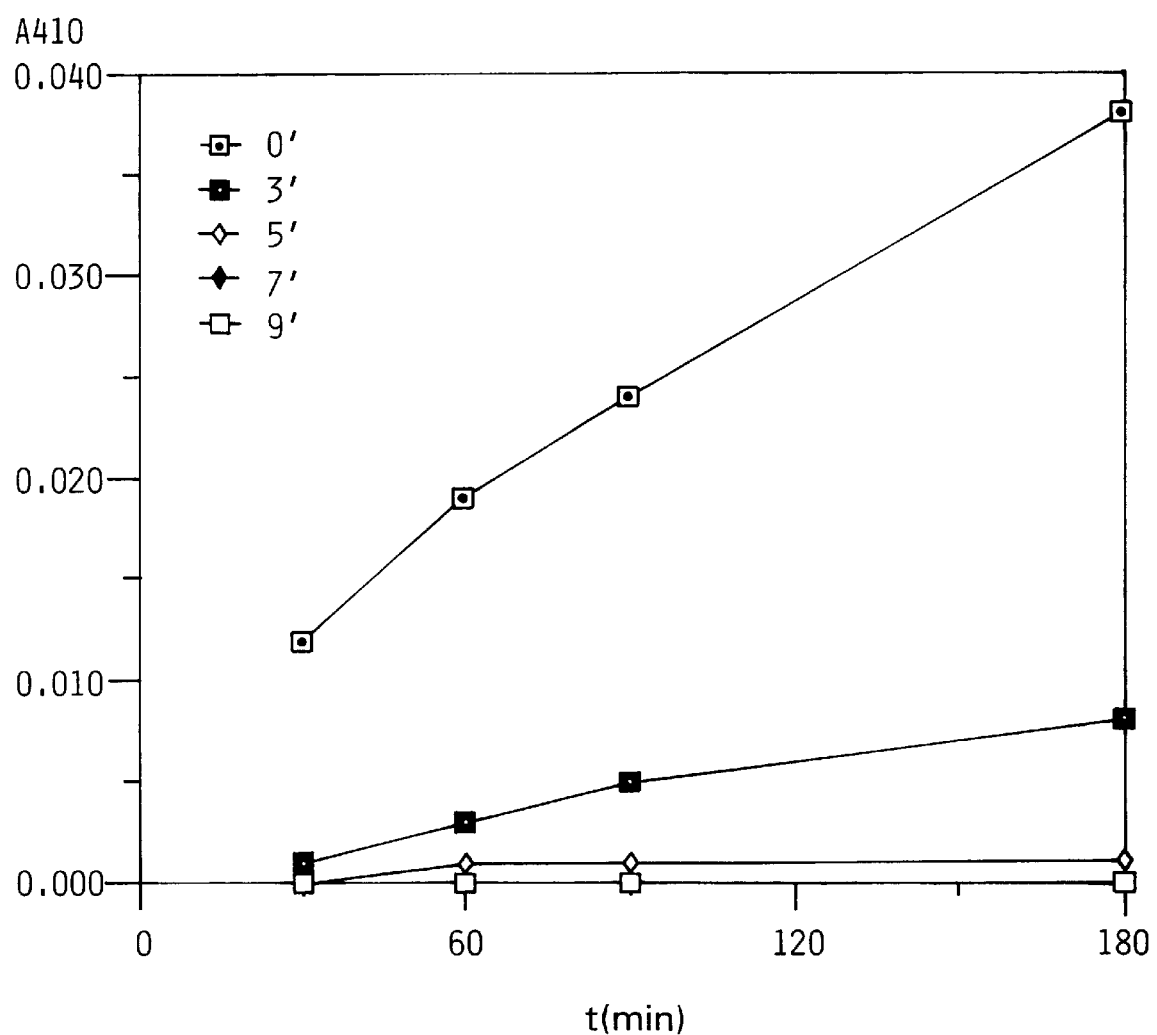
FIG. 4 is a graph of absorbance values measured over time in a protease activity assay of samples of diluted stock solution of alkaline protease heated at 67° C. for 0, 3, 5, 7, or 9 minutes.

FIG. 3 shows the relative activity of alkaline protease remaining in each of the four test samples generated by pooling and then heating aliquots of the isolated DNA samples from Example 5, above. FIG. 4 shows the relative activity of alkaline protease remaining in the control samples generated by heating a solution of the alkaline protease used in Example 5. Both figures show that the activity of the alkaline protease was reduced by at least 50% of its initial value after only three minutes of heating at 67° C., regardless of whether the protease was present in an isolated DNA sample or in a diluted stock solution of protease. Both figures also demonstrated that the alkaline protease activity in the samples tested herein was essentially undetectable within 5 minutes of heating at 67° C. The two figures (FIG. 3 and FIG. 4) are very similar to one another, indicating that none of the materials present in the isolated DNA solution, which are not present in the protease controls, had any noticable effect on the stability or instability of the alkaline protease in that solution.

This example demonstrates that essentially all of the proteolytic activity in a sample of isolated nucleic acid can be eliminated by heating the solution for 5 minutes or more at 67° C. Thus, if even small amounts of residual protease are of concern to the user, the residual protease activity in the sample can be removed by such heat inactivation.

Example 8
Flourescent Sequencing of Isolated Plasmid DNA

This example describes results obtained from the use of fluorescent sequencing of plasmid DNA isolated according to the embodiment of the method of this invention described in Examples 1 and 2, above. The assay examines the sequence of the isolated plasmid DNA to ensure the sequence was not altered or degraded during the isolation process. Fluorescent sequencing also tends to be more sensitive to contaminants in solution. For example, some contaminants can quench the fluorescent signal of one or more of the dyes used in fluorescent sequencing, while other contaminants such as nucleases can shorten or degrade template or copied strands of nucleic acids, resulting in high backgrounds and/or inaccurate results.

In this example, plasmid pGEM®-3Zf(+) DNA was isolated from 1.5 ml cultures of *E. coli* strain DH5α (an endA1 strain) in six replicates for preparations that used 10 µl of an alkaline protease solution containing 15 mg/ml of the protease as described in Examples 1 and 2. The plasmid DNA was eluted with water. Aliquots containing 1 µg of purified plasmid DNA were dried by vacuum and resuspended in 6 µl of water.

Sequencing reactions were performed with a Perkin Elmer/Applied Biosystems ABI PRISM™ Dye Primer Cycle Sequencing Ready Reaction Kit with AmpliTaq® DNA Polymerase, FS as described in the manufacturer's protocol (P/N 402113 Revision B, August 1995). The kit includes Ready Reaction Premixes that contain fluorescently-labeled sequencing primers, nucleotides, buffer and sequencing enzyme. Briefly, 1 µl of the plasmid preparations was combined with 4 µl of the A Ready Reaction Premix. A second 1 µl aliquot was combined with 4 µl of the C Ready Reaction Premix. A third 2 µl aliquot was combined with 8 µl of the G Ready Reaction Premix. A fourth 2 µl aliquot was combined with 8 µl of the T Ready Reaction Premix.

The samples were incubated in a Perkin Elmer Model 9600 thermal cycler as recommended in the manufacturer's protocol. (Perkin Elmer Protocol, Part No. 402113, Revision B, August 1995.) The cycling profile consisted of 96° C. for 10 sec., then 55° C. for 5 sec. followed by 70° C. for 60 sec. This cycling profile was repeated for 15 cycles. The samples were then subjected to 96° C. for 10 sec., then 70° C. for 60 sec. This cycling profile was repeated for 15 cycles. Samples were then incubated at 4° C. until ready to concentrate.

The cycled A, C, G and T reactions from each sample were pooled and precipitated as described in the manufacturer's protocol, cited above. The samples were washed once with 250 µl of 70% ethanol and briefly dried, as recommended. The dried pellets were resuspended in 6 µl of sample loading buffer (5 parts deionized formamide/1 part 25 mM EDTA, pH 8.0 with 50 mg/ml Blue dextran). A 1.5 µl aliquot of each sample run on a 4% urea/polyacrylamide gel and fluorescent signal data collected during the run, using a Perkin Elmer/Applied Biosystems Model 377 fluorescent DNA sequencer, using run conditions recommended by the manufacturer. Data collection was performed for three hours, after which the data was compared to the published sequence of pGEM®-3Zf(+).

All six samples yielded sequence data that was greater than 99% accurate over 500 bases without any attempt to resolve ambiguities. The resulting sequence data also showed no detectable background and no erroneous bands, indicating that the isolated samples of plasmid DNA were not contaminated by nucleases or by other similarly deleterious contaminants which adversely affected the quality of the sequence data. Table 2, below, summarizes the accuracy of the fluorescent sequencing results obtained from each of the six samples isolated and analyzed as described above.

TABLE 2

| Sample | Miscalls and N's over 500 bases | Percent accuracy |
| --- | --- | --- |
| 1 | 4 | 99.2 |
| 2 | 1 | 99.8 |
| 3 | 3 | 99.4 |
| 4 | 2 | 99.6 |
| 5 | 1 | 99.8 |
| 6 | 3 | 99.4 |

The center column of Table 2, above, lists the number of times the automated sequencer made one of two errors. The first such error, the error referred to as a "miscall" in the table above, occurs whenever the fluorescent sequencing machine read the identity of a base at a particular position as one thing, when the actual base one would expect to find at that position is another, based on the known plasmid sequence. The other such error occurs whenever the fluorescent sequencing machine is unable to determine the identity of a base at a particular location, in which case the machine read the base as unknown and inserts an "N" in place of a base at that point.

Example 9
Use of Isolated Plasmid DNA in Transfection

This example demonstrates that the method of this invention can be used to produce transfection quality DNA. In this example, pGL3-Control plasmid DNA, commercially available from Promega Corporation, was isolated from *E. coli* DH5α bacteria cells (an endA1 strain), and used to transfect two different types of mammalian cell cultures, chinese hamster ovary (CHO) cells and a culture of human cervical cancerous (HeLa) cells. Two different versions of the method of the present invention were used to isolate plasmid DNA, both of which are slightly different from the isolation method used in Examples 1 and 2, above. Like the method of Examples 1 and 2 above, the present example uses alkaline protease treatment and a resin matrix of silica particles bound to a membrane component of a spin basket assembly to isolate plasmid DNA. The specific isolation procedures used herein are outlined in the first section, below.

Only highly purified DNA can efficiently transfect tissue culture cells, such that the cells produce proteins encoded for by the genes of the DNA used to transfect the cells. Two factors in particular can affect the ability of a solution of target DNA to transfect tissue culture cells. The first is solution purity. Contaminants in the solution can cause cell death or inhibit the uptake of target DNA by the cells. The second factor is target DNA degradation, such as degradation by nuclease. In order to ensure a solution of DNA is of sufficient purity and sufficiently intact to use in transfections, a long, hazardous, and arduous two fold cesium chloride (2× CsCl) gradient centrifugation isolation procedure is traditionally used. (see, e.g., Current Protocols in Molecular Biology 9.1.1). The traditional 2× CsCl gradient method takes over forty eight hours to complete, and uses toxic chemicals, including a potent nutagen, ethidium bromide. In contrast, the procedure used in this example takes less than two hours, and uses relatively nonhazardous chemicals.

A. Preparation of Plasmid DNA Samples

Four samples of pGL3 plasmid DNA were prepared from *E. coli* DH5 alpha transformed cells, for use in the transfection procedure, discussed below. The first three samples were produced using the alkaline protease method described below, followed either by concentration by precipitation with alcohol (Sample 1) or by further isolation and concentration (Samples 2 and 3). The fourth sample (Sample 4) was produced using the traditional 2× CsCl gradient centrifugation procedure described above.

The general isolation procedure used to produce the plasmid solution of Samples 1–3 was as follows:

1. A culture of (*E. coli*) DH5 α transformed with pGL3 plasmid DNA was prepared by growing an inoculum of culture overnight in LB medium.
2. The equivalent of 3 ml of the overnight culture was centrifuged, and the cell pellets resuspended in 200 µl of resuspension solution, the same resuspension solution used in Example 1, above.
3. The cells were lysed by adding 200 µl of lysis solution to each tube of resuspended cells, and mixing the resulting lysate solution by inversion.
4. 10 µl of a 65 mg/ml solution of alkaline protease was added to the tube of lysate solution, mixed by inversion, and incubated at room temperature for five minutes.
5. The pH of each solution was lowered by adding 200 µl of neutralizing solution to the protease/lysate mixture. The composition of the neutralizing solution was the same as in Example 1, above. A precipitate formed in the solution, as soon as the acetate buffer was added.
6. The precipitate was cleared from the solution by centrifuging for 10 minutes in a microcentrifuge at room temperature.
7. A spin basket assembly was prepared by placing the basket in a 2 ml microfuge collection tube, and adding 400 µl of 7M guanidinium hydrochloride to the basket.
8. The cleared solution from step 6 was removed from each tube using a pipettor, being careful not to disturb the precipitate in each tube. About 600 µl of each such solution was transferred to the basket assembly prepared as described in step 7.
9. The spin basket assembly, loaded as described above, was then spun in a microfuge for one minute at room temperature. The basket was then removed from the collection tube, the collected solution discarded, and the spin basket placed back in the same collection tube.
10. 750 µl of wash solution (see Example 1 for the composition of this solution) was added to each spin basket after step 9, and each spin basket/tube assembly was spun in a microfuge for one minute at room temperature. The spin basket was then removed from the collection tube, and the solution collected therein discarded, in the same manner as above. The spin basket was then reinserted in the same collection tube.

11. The spin basket was washed with 250 μl of wash solution, using the same wash procedure followed in step 10. However, after this step, the spin basket was transferred to a new 1.5 milliliter microfuge tube, being careful not to transfer any of the wash solution with the basket.

12. The DNA bound to the silica membrane component of the spin basket was eluted by adding 100 μl of nuclease-free water to the basket, and by spinning the spin basket/tube assembly in a microfuge for one minute at room temperature. The spin basket was then removed from the collection tube and discarded.

13. The eluents from all the tubes of harvested cells processed herein were combined, and three aliquots of 400 μl of eluted DNA were set aside for use in preparing Samples 1, 2, and 3 as described below.

Sample 1 was prepared by concentrating the DNA in one of the 400 μl aliquots of eluted DNA. The DNA in the aliquot was precipitated out of solution by adding 100 μl of 5M sodium chloride and 350 μl of isopropanol (100%) to the aliquot of eluent. The resulting solution was centrifuged for 20 minutes at room temperature in a microfuge to pellet the precipitated DNA. The pellet was washed with 1 ml of cold 70% ethanol and air dried before being dissolved in 45 μl of TE buffer. (10 mM Tris-HCl, 1 mM EDTA, pH 8.0.)

Samples 2 and 3 were prepared as follows.
  a. 300 μl of a 2 to 1 mixture of 7M guanidine hydrochloride and 3M potassium acetate were added to 100 μl aliquots of the eluent from step 13, above. The resulting solution was added to a new spin basket, and the spin basket placed in a new 2 ml collection tube.
  b. The loaded spin basket was processed, washed, and the DNA bound thereto eluted, pooled and aliquotted into 400 μl samples by repeating steps 9 through 13, above.
  c. The DNA in each 400 μl of eluent was concentrated by precipitation with isopropanol, following the same procedure used to concentrate the DNA in Sample 1, above.

Samples 2 and 3 were both prepared as described above, but each was prepared separately. Both samples were used to transfect each of the two types of tissue culture cells tested in this example.

Sample 4 was also prepared from (*E. coli*) DH5 α cells transformed with pGL3 plasmid DNA. However, the traditional 2x CsCl gradient centrifugation procedure described above was used instead of any aspect of the isolation method of the present invention. ps B. Transfection—Calcium Phosphate Method The mammalian cell lines used in this example are Chinese Hamster Ovary (CHO) and Human (HeLa). The cells were cultured in F-12 Ham medium plus 10% fetal bovine serum—5% $CO_2$ for CHO and the HeLa cells in Dulbecco's Modified Eagles Medium (DMEM) plus 10% fetal bovine serum—10% $CO_2$. The cells were plated in 24 well dishes in appropriate media and the following procedure was followed.

1. The cells were placed in 24 well dishes, about 50,000 cells per well, approximately 24 hours before initiating transfection.
2. On the day of transfection, the media was removed from each well and replaced with fresh growth media (+serum) within one to three hours before initiating transfection.
3. A mixture of each of the four Samples of DNA (Samples 1–4) was prepared as follows. Enough mixture of each sample of DNA was prepared to transfect six wells of cell culture, as follows. 6 μl (about 6 μg) of DNA, 23.8 μl of calcium chloride, and 160 μl of sterile water were combined in a sterile polystyrene tube. The DNA/$CaCl_2$ mixture prepared above was added, dropwise, to 190.2 μl of Hank's Buffered Saline (HBS), while gently vortexing the HBS.
4. The HBS/DNA/$CaCl_2$ mixture was incubated for 30 minutes at room temperature, before adding 54.6 μl of the mixture to each well of cells. The mixture was added directly to the media containing serum.
5. The plates of treated cells were then returned to the incubator. The cells were fed with fresh serum the next day, using the same serum composition used in step 2, above.
6. After 48 hours, the cells were harvested by removing the growth medium and adding 100 μl of cell culture lysis reagent per well.

C. Assay of Transfection Efficiency

Cells transfected and harvested as described above were assayed to see whether the reporter gene, in this case the luciferase gene of pGL3 plasmid DNA, was expressed in the cells. A standard luciferase assay, the Luciferase Assay System commercially available from Promega Corporation, was used to detect and quantify luciferase expression in the cells.

Cells harvested in step 6, above were incubated for another 15 minutes at room temperature before being assayed for luciferase expression. An aliquot from each well of cells was then placed in a different well of a microtiter plate dish. The amount of luminescence emanating from each well was detected and quantified using a luminometer.

The two tables below summarize the results obtained from the four aliquots of each of the two types of cell culture transfected with each of the four Samples of pGL3 DNA prepared as described above. Table 3 summarizes the results of the HeLa transfections, while Table 4 summarizes the results of the CHO transfections.

TABLE 3

| HeLa | Sample 1 | Sample 2 | Sample 3 | Sample 4 |
|---|---|---|---|---|
| Luminescence | 92.32 | 176.5 | 235.6 | 450.3 |
| Detected | 180.9 | 186.7 | 303.4 | 392.9 |
| (in Turner | 162.6 | 165.5 | 269.2 | 376.91 |
| Light Units) | 185.2 | 164.3 | 281.8 | 396.6 |
| ave | 155 | 173 | 273 | 404 |
| std dev | 43 | 111 | 28 | 32 |

TABLE 4

| CHO | Sample 1 | Sample 2 | Sample 3 | Sample 4 |
|---|---|---|---|---|
| Luminescence | 3214 | 14050 | 7537 | 7972 |
| Detected | 4743 | 8827 | 10982 | 9129 |
| (in Turner | 4004 | 9398 | 10974 | 16416 |
| Light Units) | 8006 | 5631 | 5277 | 6428 |
| ave | 4992 | 9477 | 8693 | 9986 |
| std dev | 2104 | 3470 | 2796 | 4427 |

The results above demonstrate that the method of this invention can be used to produce transfection quality DNA. The results show, specifically, that when Samples 1–3 were used to transfect cells of two different types of mammalian cell cultures, the resulting cells expressed the luciferase reporter gene as did cells transfected with Sample 4 DNA, in which the traditional 2× CsCl gradient centrifugation procedure was used. In other words, DNA isolated by the traditional 2× CsCl method was transfected into the cells with a similar efficiency to DNA isolated using the specific version of the alkaline protease isolation method described in this example above.

Example 10
Treatment of a Nucleic Acid Solution

A nucleic acid solution is treated with an alkaline protease substantially to inactivate any proteins in the solution capable of degrading the nucleic acid material or of interfering with use of the nucleic acid material for transfection or other useful applications disclosed herein above. The nucleic acid solution treated in this example is either a solution of nucleic acid material isolated by any known isolation procedure, wherein the resulting solution contains, or is suspected to contain, such deleterious proteins, or a nucleic acid solution produced by suspending and lysing a biological material using one of the methods of suspension and lysis described herein above.

The nucleic acid solution is treated by adjusting the pH of the solution to an alkaline pH, followed by incubating the solution in the presence of alkaline protease until deleterious proteins in the solution are substantially inactivated, and then lowering the pH of the solution to a pH wherein the alkaline protease is less active, e.g., by lowering solution pH to at least a neutral pH.

Substantial inactivation of proteins capable of degrading the nucleic acid material is determined as follows. First, two aliquots of nucleic acid solution samples are prepared, with a 1× core buffer solution containing magnesium such as that described above, and the other without core buffer. The sampler are then incubated overnight at 37° C. The composition of the core buffer is the same as described in Example 3, above. Second, the incubated samples are fractionated on a 1% agarose gel in Tris-acetate-EDTA electrophoresis buffer containing 0.5 mM iodopropyl thiazole orange. Third, the gel of fractionated samples is scanned using a fluorescent scanner such as a FluorImager (Molecular Dynamics) to visualize the fractionated nucleic acid material in the gel. The banding pattern produced from fractionating the sample containing core buffer is compared to the sample lacking core buffer. Proteins capable of degrading the nucleic acid material in the solution are substantially inactivated if the banding pattern produced from the sample containing core buffer is substantially identical to the pattern produced from the sample lacking core buffer. Two banding patterns are substantially identical to one another where the number and approximate positioning of the bands in the gel are the same, where the relative intensity of all the bands of each pattern is the same, and where neither banding pattern includes smears or fuzziness corresponding to smaller molecular weight sizes not present in the other pattern.

Substantial inactivation of proteins capable of interfering with a use of the nucleic acid material in the nucleic acid solution is determined by performing a functional test on the solution, after treatment with alkaline protease, as described above. The functional test used depends on the type of nucleic acid material in the solution, and on the particular application of interest. When the material is plasmid DNA, and the application of interest is transfection of mammalian cells, the treated solution is tested by using a sample of the solution to transfect mammalian cells, such as was done in Example 9, above. When the material is mRNA, and the application of interest is preparing a cDNA library to clone a particular gene, the treated solution is subjected to the procedure used to reverse, transcribe and clone the resulting cDNA. When the material is human genomic DNA, and the application is human identity testing, a sample of the treated solution is used as a substrate in the identity test of interest (e.g. using a standard polymerase chain reaction, or restriction fragment length polymorphism assay).

Example 11
Treatment of a Solution of RNA Extracted From a Biological Material

RNA is isolated from a biological sample, such as mammalian tissue, by the following procedure: The biological sample is homoenized in the presence of a high concentration of a chaotropic salt, such guanidine thiocyanate. An acid buffered mixture of phenol and chloroform is then added to the resulting lysate, and used in an organic extraction. When the lysate solution is subjected to organic extraction, any RNA in the solution partitions into the aqueous phase, and contaminants such as DNA and denatured and inactivated proteins partition (Cold Spring Harbor, Publisher) into the organic phase and interphase layers, respectively. A single organic extraction step, however, does not effectively remove or inactivate all of the contaminating nucleases in the solution which are capable of degrading RNA in RN are rich tissues such as pancrese. In order to avoid multiple additional extraction steps to remove or inactivate residual nucleases and other deleterious proteins remaining in solution, the aqueous phase from an organic extraction step, preferably from the first organic extraction step, is envisioned to be treated with alkaline protease as follows: The pH of the aqueous extract is adjusted to an alkaline pH ranging between 7 and 9 a pH sufficiently high for the alkaline protease to be activated but not so high as to hydrolyze the RNA. A solution containing alkaline protease is added and the resulting alkaline extract solution is then incubated at room temperature for at least 5 minutes. The length of incubation time and the alkaline protease concentration used are sufficient to ensure substantial inactivation of residual ribonuclease in the solution. Substantial inactivation of ribonuclease is determined by either reverse transcription and cDNA production, PCR of the RNA example, or agarose gel electrophoresis in the presence of formaldehyde as described in Maniatis/Gambrook, *Current Protocols in Molecular Biology*.

Example 12
Isolation of RNA From Protease Treated Extract

RNA is isolated from the aqueous extract treated with alkaline protease in Example 11, using a silica resin matrix, as follows. The treated aqueous extract solution contains a high concentration of chaotropic salt. This solution is diluted with nuclease free water to a chaotropic salt concentration range known to promote binding of RNA to a matrix of silica particles. The diluted solution is then placed in contact with a silica resin matrix, under conditions designed to allow the RNA to bind to the matrix. The matrix is then washed at least once with a wash solution comprising at least 50% alcohol and a medium ionic strength aqueous solution, such as a wash solution consisting of 0.01M NaCl, 0.01M Tris-HCl (ph 7.5), and 80% ethanol. The RNA is eluted from the matrix using nuclease-free water or an aqueous buffer of low ionic strength, such as TE buffer (see Example 9, above, for the composition of TE buffer). A solution of alkaline protease is then added to the RNA and incubated in order to allow the protease to digest any ribonuclease present in the RNA solution. The amount of protease needed can be determined as in Example 11.

We claim:
1. A method for treating a nucleic acid solution with an alkaline protease, the nucleic acid solution comprising a nucleic acid material and proteins, the method comprising:

(a) adjusting the pH of the nucleic acid solution to a pH of at least about 10, thereby forming an alkaline nucleic acid solution;
(b) incubating the alkaline nucleic acid solution in the presence of an alkaline protease, until the proteins are substantially inactivated; and
(c) lowering the pH of the solution sufficiently to reduce protease activity.

2. The method of claim 1, wherein the proteins substantially inactivated in the incubating step (b) of the method are capable of degrading the nucleic acid material.

3. The method of claim 1, wherein lowering the pH of the solution in step (c) results in the formation of a precipitate, and wherein the precipitate is removed by centrifugation.

4. The method of claim 1, wherein the nucleic acid material is DNA, and wherein the proteins inactivated in step (b) of the method comprise nucleases capable of degrading DNA.

5. The method of claim 1, wherein the alkaline nucleic acid solution formed in step (a) of the method is an alkaline lysate solution, and wherein alkaline protease is added to the solution before incubation.

6. The method of claim 5, further comprising forming the alkaline lysate solution by:
suspending a biological sample in a solution, the biological sample comprising the nucleic acid material and the proteins; and
adjusting the pH of the solution of suspended sample to the pH of at least about 10 by adding an alkaline lysis solution, the alkaline lysis solution comprising a base and an anionic detergent.

7. A method for isolating nucleic acid material from a biological sample comprising protein material and nucleic acid material, the method comprising:
(a) suspending the biological sample in a solution;
(b) adjusting the pH of the solution to a pH of at least about 10 by adding an alkaline lysis solution, thereby forming an alkaline lysate solution;
(c) incubating the alkaline lysate solution in the presence of an alkaline protease, until proteins capable of degrading the nucleic acid material are substantially inactivated;
(d) lowering the pH of the alkaline lysate solution sufficiently to reduce protease activity.

8. The method of claim 7, wherein the solution used to suspend the biological sample comprises water, a buffer and a chelating agent.

9. The method of claim 7, wherein the nucleic acid isolated is a DNA material, the method further comprising the step of incubating the sample in the presence of an ribonuclease enzyme until any RNA in the sample is substantially degraded.

10. The method of claim 7, wherein the nucleic acid isolated is a DNA material, and wherein the alkaline lysis solution added to the suspension solution in step (b) comprises sodium hydroxide and an anionic detergent.

11. The method of claim 7, wherein the pH of the alkaline lysate solution is lowered in step (d) by adding an acidic solution comprising an acetate buffer of pH between 3.5 and 4.5.

12. The method of claim 7, wherein lowering the pH of the alkaline lysate solution in step (d) results in the formation of a cloudy lysate solution, and further comprising the step of clearing the cloudy lysate, thereby forming a cleared lysate solution.

13. The method of claim 12, wherein the cleared lysate solution is formed by centrifuging the cloudy lysate solution.

14. The method of claim 12, further comprising isolating the nucleic acid material from other materials in the cleared lysate solution, using alcohol precipitation.

15. The method of claim 12, further comprising isolating the nucleic acid material from other materials in the cleared lysate solution, using paramagnetic particles.

16. The method of claim 12, further comprising isolating the nucleic acid material from other materials in the cleared lysate solution, using a resin matrix comprising silica particles.

17. The method of claim 16, wherein the nucleic acid material is DNA, wherein the resin comprises silica, wherein a chaotropic agent is used to reversibly bind the DNA to the resin, wherein the resin is rinsed with a wash solution to remove other material in the mixture, and wherein after rinsing an elution buffer or water is used to release the DNA from the resin.

18. The method of claim 7, further comprising the step of heat inactivating the alkaline protease after lowering the pH of the mixture in step (d).

19. A method for isolating DNA material from a biological sample comprising the DNA material and protein material, the method comprising:
(a) suspending the biological sample in an aqueous solution, the solution comprising ribonuclease and buffer;
(b) adjusting the pH of the solution to at least about pH 10 by adding an alkaline lysis solution comprising an anionic detergent and a base, thereby forming an alkaline lysate solution;
(c) adding an alkaline protease to the alkaline lysate solution, forming a protease/lysate mixture;
(d) incubating the mixture until proteins capable of degrading the nucleic acid material are substantially inactivated;
(e) lowering the pH of the mixture by adding an acidic solution, wherein addition of the acidic solution results in the formation of a cloudy lysate;
(f) clearing the cloudy lysate by centrifugation; and
(g) isolating the DNA material from other material in the cleared lysate.

20. The method of claim 19, wherein the solution used to suspend the biological sample further comprising a buffer and a chelating agent.

21. The method of claim 19, wherein the acidic solution used to lower the pH of the mixture comprising an acetate buffer of pH between 3.5 and 4.5.

22. The method of claim 19, wherein the DNA material is isolated from the cleared lysate using a resin matrix comprising silica particles, wherein the resin matrix is capable of reversibly binding the nucleic acid material.

23. The method of claim 22, the method additionally comprising the steps of:
(h) adding the cleared lysate and a chaotropic agent to the resin matrix, thereby binding the DNA material to the resin matrix;
(i) rinsing the resin matrix at least once with a wash solution;
(j) using an elution buffer or water to release the DNA material from the resin matrix.

24. The method of claim 19, further comprising the step of heat inactivating the alkaline protease after lowering the pH of the mixture in step (e).

* * * * *